US009505023B2

(12) United States Patent
Schaefer et al.

(10) Patent No.: US 9,505,023 B2
(45) Date of Patent: Nov. 29, 2016

(54) OZONE APPLICATOR AND METHOD FOR POLYMER OXIDATION

(75) Inventors: Suzanne E. Schaefer, Appleton, WI (US); Jeremy Lee Winsor, Appleton, WI (US); Paul V. Zeyn, Joplin, MO (US)

(73) Assignee: COVERIS FLEXIBLES US LLC, Chicago, IL (US)

( * ) Notice: Subject to any disclaimer, the term of this patent is extended or adjusted under 35 U.S.C. 154(b) by 724 days.

(21) Appl. No.: 12/922,202

(22) PCT Filed: Mar. 13, 2009

(86) PCT No.: PCT/US2009/037138
§ 371 (c)(1),
(2), (4) Date: Apr. 13, 2011

(87) PCT Pub. No.: WO2009/114794
PCT Pub. Date: Sep. 17, 2009

(65) Prior Publication Data
US 2011/0183074 A1 Jul. 28, 2011

Related U.S. Application Data

(60) Provisional application No. 61/036,760, filed on Mar. 14, 2008.

(51) Int. Cl.
| | |
|---|---|
| *G03C 1/76* | (2006.01) |
| *B05D 1/30* | (2006.01) |
| *C07D 417/12* | (2006.01) |
| *C07D 417/14* | (2006.01) |
| *B05D 3/04* | (2006.01) |

(52) U.S. Cl.
CPC ............ *B05D 1/305* (2013.01); *C07D 417/12* (2013.01); *C07D 417/14* (2013.01); *B05D 3/044* (2013.01)

(58) Field of Classification Search
None
See application file for complete search history.

(56) References Cited

U.S. PATENT DOCUMENTS

| | | | | |
|---|---|---|---|---|
| 2,872,397 A | * | 2/1959 | Kiffer | ............ B01D 53/04 204/176 |
| 4,499,853 A | * | 2/1985 | Miller | ............ 118/725 |
| 4,778,380 A | | 10/1988 | Nitta | |
| 5,003,777 A | | 4/1991 | Berchowitz | |
| 5,503,968 A | * | 4/1996 | Lee | ............ 430/532 |
| 5,705,110 A | * | 1/1998 | Weber | ............ B29C 41/04 264/310 |
| 6,106,659 A | | 8/2000 | Spence et al. | |
| 6,171,625 B1 | | 1/2001 | Denvir et al. | |
| 6,702,941 B1 | | 3/2004 | Haq et al. | |
| 2002/0057422 A1 | * | 5/2002 | Arakawa | ............ G03F 7/70525 355/30 |
| 2002/0187333 A1 | * | 12/2002 | Gu | ............ B29C 33/68 428/308.8 |
| 2008/0061006 A1 | | 3/2008 | Kerfoot | |

OTHER PUBLICATIONS

International Search Report and Written Opinion dated Apr. 27, 2009 relating to PCT International Application No. PCT/US2009/037138.

* cited by examiner

*Primary Examiner* — Mandy Louie
(74) *Attorney, Agent, or Firm* — Stoel Rives LLP (57) ABSTRACT

Apparatuses and methods are described for distributing gas which may be applicable in the field of polymer oxidation and melt curtain ozonation in particular. Ozone applicators and other features of ozonation apparatuses, which may be used separately or in combination, are also described.

7 Claims, 6 Drawing Sheets

OZONE APPLICATOR AND METHOD FOR POLYMER OXIDATION

FIELD OF THE INVENTION

The present invention relates to apparatuses and methods for distributing gas which may be applicable in the field of polymer oxidation and melt curtain ozonation in particular. Aspects of the invention relate to ozone applicators as well as other features of ozonation apparatuses and associated methods.

BACKGROUND OF THE INVENTION

The extrusion of molten polymers and copolymers, with subsequent bonding of the extruded polymer film or "curtain" onto a substrate, is well known. The process normally involves melting the polymer in an extruder, extruding the molten polymer through a die to form the melt curtain, and passing the substrate (e.g., paper or aluminum foil) and the extruded film simultaneously between two pressure rolls to bond the hot polymer film and the substrate. In a typical operation, plastic resin pellets are melted and extruded through a narrow (e.g., 0.030 inch) linear die opening to form the melt curtain or molten plastic web. Various polymers suitable for extrusion coating include polyolefins (e.g., polyethylene), olefinic copolymers (e.g., ethylene-propylene or ethylene-acrylic acid copolymers), and olefinic polymer blends (e.g., a blend of polypropylene with either polyethylene or polystyrene).

Extrusion coating is described in detail, for example, in U.S. Pat. No. 4,183,845 and WO 2002/094556. The process may be used in a number of applications, for example in the preparation of labels and decals or packaging materials such as those used in food packaging.

The adhesion of the molten polymer to the extrudate can be significantly improved with ozone application to the side of polymer melt curtain that contacts the substrate, or otherwise contacts an intermediate layer that adheres to the substrate. In particular, a discharge of ozone in the vicinity of the molten polymer, shortly before it contacts the substrate, provides controlled oxidation on the bonding or "preferred" side of the extrudate. The process known as melt curtain ozonation therefore provides bonding sites on the molten polymer which promote oxidative type bonding.

Good polymer/substrate adhesion and consequently minimal delamination is critically dependent on the manner in which ozone is applied. Also, the close proximity between the equipment from which ozone is applied (i.e., the ozone applicator) and the molten polymer renders this equipment subject to plugging and/or to becoming caked or coated, both internally and externally, with the polymer or polymer byproducts. This results in uneven ozone distribution and consequently poor adhesion of the finished laminate. Frequent cleaning (e.g., at approximately six-week intervals) of the ozone applicator is therefore often mandatory to combat the deposition and condensation of polymer, both onto and into, the ozone applicator, due to its contact with molten polymer or polymer vapors.

Thus, there remains a need in the art for improved gas distributors such as ozone applicators, as well as ozonation apparatuses and methods, which can improve the application of ozone in melt curtain ozonation, thereby reducing polymer/substrate delamination as well as the detrimental effects, including decreased operating efficiency, associated with polymer deposition on the ozone applicator.

SUMMARY OF THE INVENTION

The present invention is associated with the discovery of improved apparatuses and methods of discharging gas, especially ozone-containing gas used in melt curtain ozonation, as discussed above. The apparatuses and methods advantageously improve ozone distribution across the width of the molten polymer film, resulting in enhanced bonding between the polymer and substrate and consequently reduced delamination in the end product laminate, even for relatively wide laminate sheets. Also associated with the apparatuses and methods of present invention is a reduction in the extent of polymer or polymer byproduct and vapor deposition onto or inside of the ozone applicator during melt curtain ozonation.

Aspects of the invention therefore relate to an ozone applicator that provides improved distribution of discharged gas, such as ozone-containing gas that is a mixture of ozone gas and a diluent (e.g., air). According to one embodiment, the applicator, or applicator bar, includes elongated, inner and outer shells with the inner shell disposed within the outer shell. The shells may therefore be, for example, nested cylinders with the inner diameter of the outer shell exceeding the outer diameter of the inner shell such that an intermediate (e.g., annular) space is formed between the shells. Other shell geometries are possible and could similarly result in the formation of an intermediate space.

An inlet stream of gas such as ozone-containing gas flows, or is received, into the interior or innermost space that is surrounded by the inner shell. The gas then flows into the intermediate space through at least one opening such as an elongated aperture (e.g., having an oval shape), or in some cases through a plurality of holes, on the inner shell that allow fluid communication between the interior and intermediate spaces. These one or more elongated apertures or holes (or openings having other shapes) may be distributed along at least a portion of the length of the inner shell. The gas in the intermediate space then exits, or is discharged from, the applicator through at least one outlet on the outer shell that allows fluid communication between the intermediate space and the exterior of the applicator. This outlet may be, for example, in the form of a plurality of holes, or otherwise an elongated slot that extends longitudinally (axially) along at least a portion of the length of the outer shell.

Advantageously, in the inner/outer shell arrangement described above, the opening or plurality of openings of the inner shell do not align with the outlet of the outer shell. That is, the gas flow through the inner shell opening(s) does/do not coincide with the gas flow through the outer shell outlet (e.g., in the form of a plurality of openings), and typically these flows are in different directions. In many cases, it may be desired to configure the applicator such that the flow through the inner shell opening(s) is/are opposite (at a 180 angle relative to) or substantially opposite (at a 160-200 degree angle relative to) the flow through the outer shell outlet or discharge opening(s). Therefore, the inner shell opening or openings may be aligned substantially opposite the outer shell outlet.

In this manner, the change in direction of the ozone-containing gas flow through the inner and outer shells can provide a more tortuous or complicated pathway through the ozone applicator and greatly improve distribution of the exiting or discharged gas along its length (e.g., through a plurality of holes or an elongated outlet slot). Variations in the ozone-containing gas flow exiting the applicator bar and contacting the melt curtain are minimized across the applicator bar length and consequently the melt curtain width, even at peripheral or outermost locations.

In another embodiment, the ozone applicator comprises only a single elongated shell that surrounds the interior space from which an inlet stream of ozone-containing gas is received. In this case, the shell as a plurality of openings that are disposed about a portion of the shell surface (e.g., a cylindrical surface portion) that extends longitudinally (or axially, i.e., parallel to the shell axis) but that is confined to an arcuate section within about 90° ($\pi$/2 radians), and often within about 45° ($\pi$/4 radians), based upon an arc of a cross-sectional shape (e.g., a circle) of the shell. The openings may be disposed, for example, over an arcuate section of a cylindrical surface, with the arc ranging from about 10° ($\pi$/18 radians) to about 60° ($\pi$/3 radians), or otherwise disposed over an arcuate section with an arc of about 40° (2$\pi$/9 radians). For example, the openings may be holes disposed in longitudinally extending, substantially parallel lines that are separated by an arc angle as described above. In a particular embodiment, two separate, spaced-apart lines of holes extend over a portion (e.g., from about 30% to about 80%) of the shell length, which may be centered over this length, in a staggered conformation such that the holes of one line are in different axial positions relative to holes in the other line.

Gas distributors and particularly ozone applicators as described above provide a uniformly distributed flow of gas across the length of the applicator bar (and consequently the width of the melt curtain). This improvement in flow distribution is especially significant for applicator bar lengths of at least about 61 centimeters (at least about 24 inches), where gas distribution difficulties become significantly more pronounced in the case of conventional ozone applicators.

Exposing a polymer surface (e.g., an essentially flat surface of a molten extrudate) to ozone discharged from any of the ozone applicator bars described above therefore results in more uniform or even oxidation of the polymer and consequently improved adhesion of the polymer to a substrate, relative to the performance obtained from conventional apparatuses and methods. This improves laminate product quality, especially in the production of wide laminates. Also, compared to conventional applicators, the applicator bar configuration described herein advantageously allows a higher overall gas flow rate to be discharged through the bar, without causing pressure to increase within the ozonation apparatus to a level that could damage key equipment (e.g., dielectric tubes inside the ozone generator) used to generate ozone. These higher gas flows that can be achieved using the applicator described above also beneficially improve ozone distribution and substrate bonding.

Other aspects of the invention relate to modifications of ozonation apparatuses and particularly those used in melt curtain ozonation, as well as the resulting ozonation processes that result from these modifications. The modifications are associated with ensuring a constant feed of diluent gas (e.g., a substantially non-ozone containing gas such as air) through the ozone applicator. In particular, the use of a continuous supply of diluent gas during the entire melt curtain ozonation process (including non-normal operating periods such as startup and upset conditions, when ozone gas is not flowing through the applicator), provides commercial advantages. Importantly, the rate of accumulation (or build-up) of unwanted polymer or polymer byproduct inside of or on top of the applicator bar, due to its proximity to molten polymer and polymer vapors, is dramatically reduced. Such solids can adhere both within the applicator as a condensate, as well as on external surfaces of the applicator, as a coating or caked material.

Apparatuses and methods for performing polymer oxidation such as melt curtain ozonation are therefore associated with the discovery of advantages resulting from maintaining an essentially continuous or constant gas flow (i.e., a source of positive pressure), exiting the ozone applicator to minimize or prevent its contact with polymer or polymer vapors. These advantages include improved operating efficiency resulting from increased run time (i.e., less operational downtime associated with cleaning the ozonation equipment). Moreover, reducing blockage of the ozone applicator interior spaces and outlet by vapor and liquid polymer, respectively, prevents loss of the desired, well-distributed gas flow from the applicator outlet, as required for good polymer/substrate adhesion.

Accordingly, modifications of the melt curtain ozonation apparatuses, relative to conventional equipment, include piping, tubing, or other conduit connections that allow air or other diluent gas to be constantly fed to the ozone applicator. Therefore, rather than combining or mixing diluent gas and ozone gas prior to a valve or other device that diverts the entire, combined ozone-containing gas stream away from the applicator inlet (i.e., interrupts the entire gas flow to the applicator), the diluent gas is added downstream of such a device. For example, diluent air may be added to the ozone applicator through a jet pump, with the outlet of this pump combining with ozone gas downstream of a diverter valve that redirects the ozone gas to a rooftop mounted ozone destruct unit prior to venting.

The minimization or prevention of "no-flow" situations (e.g., during startup or upset conditions) or the substantial loss of gas flow through the applicator, when in proximity to molten polymer, greatly improves melt curtain ozonation processes. In particular, modifications to maintain continuous gas flow through the ozone applicator have dramatically reduced the extent to which polymer vapors condense within the inside of, or polymer adheres to the outside of, the applicator. Blockage of even a portion of the flow through the applicator (e.g., a portion of an outlet slot) prevents effective, well-distributed ozonation of polymer in melt curtain ozonation processes and adversely impacts polymer adhesion to the substrate. Frequent cleaning of the applicator to remove deposited polymer greatly reduces operating efficiency.

A further advantage of such flow routing modifications to conventional melt curtain ozonation apparatuses is that the amount of added diluent gas such as air, used to distribute ozone-containing gas across the length of the applicator, can be increased with only a relatively small impact on the reactor pressure within the ozonator. The modifications thus improve the efficiencies of ozone gas production and flow, ozone gas deliverability to the applicator, product quality, and production quantity. The modifications additionally reduce waste and machine downtime for cleaning, without the negative aspects of increased reactor pressure and hardware contamination.

Aspects of the invention are therefore directed to a melt curtain ozonation apparatus comprising an ozone gas conduit (e.g., comprising piping and/or tubing) that flows ozone gas from an ozone generator to an ozone applicator. The apparatus further comprises a device that allows interruption or diversion of ozone gas flow to the ozone applicator, where the device acts on the ozone conduit (i.e., is in fluid communication with the ozone gas stream) between the ozone generator and the ozone applicator. A diluent gas conduit for flowing diluent gas to the ozone applicator intersects the ozone gas conduit (i.e., provides mixing between the ozone gas and diluent gas streams) downstream of the device. The apparatus may optionally include a pressure regulator, such as a back pressure regulator, downstream pressure regulator, a pressure relief valve, etc. in order to prevent the pressure in the ozone generator from exceeding a maximum value, such as a specified maximum operating pressure.

Other aspects of the invention relate to melt curtain ozonation methods that involve flowing a mixture of ozone gas and a diluent gas into an ozone applicator, with at least a portion of the diluent gas being mixed with ozone gas downstream of a device, as discussed above, which allows interruption or diversion of ozone gas flow to the applicator. The device used may be a manually or automatically actuated valve, such as a diverter valve or a block valve, which is typically used to redirect or stop ozone gas flow during the ozonation process under certain circumstances such as startup, upset, and emergency conditions (all of which may be considered non-normal operating periods). According to these methods, therefore, ozone gas is stopped, interrupted, or diverted from the ozone applicator, in such circumstances during ozonation, without stopping or interrupting diluent gas flow. Typically, the diluent gas flow is maintained constant during any of these conditions, but it may also be desired in some cases to increase diluent gas flow to maintain a total amount of gas flow through the applicator that is equivalent to the normal flow of combined ozone gas and diluent gas. Otherwise, the diluent gas flow may also be decreased during these non-normal operating periods to a minimum value that is sufficient to prevent deposition or condensation of polymer from the melt curtain, onto or into the ozone applicator.

The advantageous features relating to ozone applicators and ozonation apparatuses, as discussed above, may be used separately. Otherwise, the use of the applicator configuration with the flow routing improvements provides a combination of benefits that can be exploited in melt curtain ozonation processes wherein a polymer in the form of a molten extrudate is oxidized.

These and other aspects and features relating to the present invention are apparent from the following Detailed Description.

The features of the apparatuses referred to in FIGS. 1-8 are not necessarily drawn to scale and should be understood to present an illustration of the invention and/or principles involved. Some features depicted in the figures have been enlarged or distorted relative to others, in order to facilitate explanation and understanding. The same reference numbers are used in the figures for similar or identical components or features shown in the various embodiments. Gas distributors such as ozone applicators, as well as melt curtain ozonation apparatuses, as disclosed herein, will have configurations, components, and operating parameters determined, in part, by the intended application and also the environment in which they are used.

DETAILED DESCRIPTION OF THE INVENTION

As used herein, for convenience, "ozone" refers to the triatomic oxygen molecule $O_3$, while "ozone gas" refers to gas generated in an ozone generator, having a substantially elevated ozone content relative to the ambient surroundings. Typically this ozone content is in the range from about 10 g/Nm$^3$ (grams per normal cubic meter) to about 1000 g/Nm$^3$. "Ozone-containing gas" refers to a mixture that results when ozone gas is mixed with a diluent gas such as air. The ozone-containing gas therefore has a lower ozone content than the ozone gas prior to mixing, typically in the range from about 2 g/Nm$^3$ to about 500 g/Nm$^3$. "Diluent gas" refers to gas that is essentially free of ozone, for example, containing less than about 5 ppm of ozone. Air is a diluent gas, as are inert gases such as nitrogen and argon. Other types of diluent gases include mixtures of air and inert gases (e.g., nitrogen-enriched air), oxygen, or oxygen-enriched air.

Figure 1:
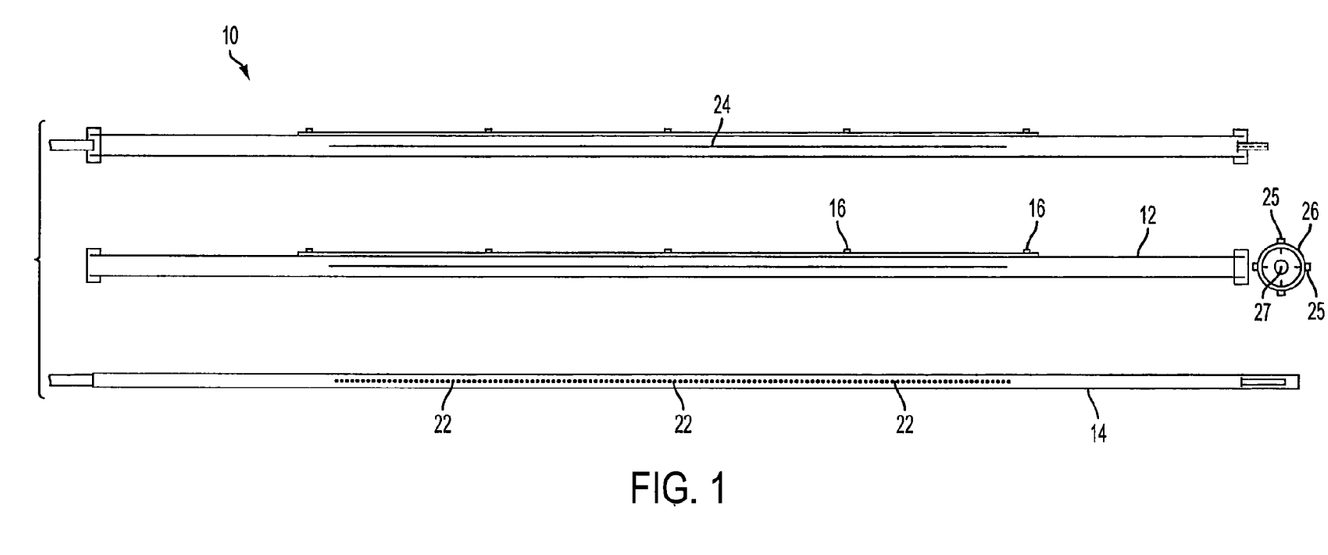
FIG. 1 depicts an ozone applicator and also separately depicts inner and outer shells of the applicator.

A representative ozone applicator 10 is depicted in FIG. 1, as well as component parts, namely an elongated outer shell 12 and an elongated inner shell 14. In the applicator or "applicator bar" 10, inner shell 14 is not visible, as it is disposed within outer shell 12. As shown, both shells 12, 14 are cylindrical with a circular cross section, but it will be appreciated that other cross-sectional geometries are possible (e.g., oval, polygonal, etc.). Typically, both shells are of approximately the same length, with shell lengths generally from about 25 to about 356 centimeters (about 10 to about 140 inches), and often from about 61 to about 356 centimeters (about 24 to about 140 inches). Because of their ability to uniformly distribute gas flow over wide widths (e.g., over wide sheets of molten polymer), applicators having lengths of at least about 61 centimeters (about 24 inches) provide considerable advantages. A representative applicator bar length is about 140 centimeters (about 55 inches).

Inner and outer shells 14, 12 may be aligned, for example using set screws 25 that are spaced apart around end cap 26. FIG. 1 illustrates a representative end cap 26 having four set screws 25 spaced evenly at 90° angles about the circumference of the edge of end cap 26 that fits over outer shell 12. The center of end cap 26 may have a receiving hole 27 allowing inner shell 14 to extend through end cap 26 and providing a fixed spatial relationship between inner shell 14 and end cap 26. Set screws 25 extend through end cap 26 to the exterior surface of outer shell 12 and allow adjustment or movement of outer shell 12 in relationship to inner shell 14 and end cap 26. Outer shell 12 may therefore be positioned around a common central axis shared with inner shell 14 (e.g., in a concentric manner) or possibly in an offset relationship (i.e., where central axes of inner shell 14 and outer shell 12 are not aligned) if desired.

Figure 2:
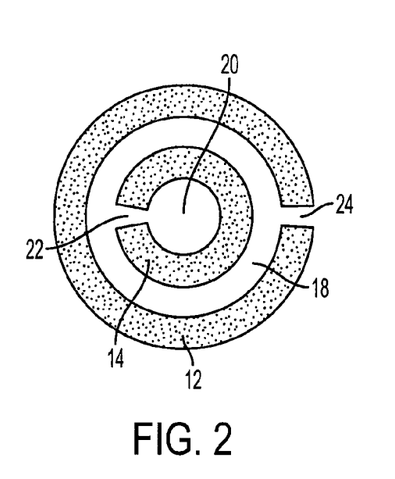
FIG. 2 depicts a cross-sectional view of an ozone applicator comprising elongated inner and outer shells.

A representative cross-section of applicator 10 is shown in FIG. 2 where outer shell 12 has an inner diameter (or other inner dimension) that exceeds the outer diameter (or other outer dimension) of inner shell 14. This allows the shells to be spaced apart from each other, so than an intermediate space 18 is formed between the shells 12, 14. In a representative embodiment, the inner diameter (i.d.) and outer diameter (o.d.) of outer shell 12 may be about 19 mm and about 25 mm (about ¾ inches and about 1 inch), respectively. Other inner and outer diameters (e.g., from about 6 mm to about 95 mm (about ¼ to about 3¾ inches) i.d. or from about 12 mm to about 102 mm (about ½ to about 4 inches) o.d.) are possible, depending on the particular application. Likewise, representative i.d. and o.d. ranges for the inner shell are from about 3 mm to about 64 mm (about ⅛ inches to about 2½ inches) and from about 6 mm to about 57 mm (about ¼ inches to about 2¼ inches), respectively, with about 6 mm (¼ inch) i.d. and about 12 mm (½ inch) o.d. being representative.

As shown in the cross-sectional view of FIG. 2, inner shell 14 surrounds an interior space 20 that receives, or is in fluid communication with, a gas stream such as an ozone-containing gas stream during normal operating conditions in a melt curtain ozonation process. After entering interior space 20, the gas stream flows from interior space 20 to intermediate space 18 through at least one opening 22 of inner shell 14. In one representative embodiment, inner shell 14 has a plurality of holes 22 (see FIG. 1) that are distributed, or extend longitudinally, along at least a portion of the length of inner shell 14. Holes 22 may otherwise extend non-linearly, for example, they may be positioned randomly or at predetermined locations about the surface of inner shell 14.

In a representative embodiment, holes 22 may extend substantially linearly and be spaced apart evenly (e.g., with centers of adjacent holes being spaced apart at an interval that can range from about 3 mm to about 6 mm (about ⅛ inches to about ¼ inches)) along a portion or section of inner shell 14 that is centered with respect to the overall length of inner shell 14. The length of this portion or section may be, for example, from about 30% to about 80%, and often from about 50% to about 70%, of the length of the inner shell. According to an exemplary embodiment where the total length of the applicator (meaning the extended length if the applicator is extendible) is about 140 centimeters (about 55 inches), the length of the section having holes may be about 84 centimeters (about 33 inches). Representative hole diameters are from about 0.8 mm to about 6 mm (about 1/32 inches to about ¼ inches), with 1.5 mm to 3 mm (1/16 inch to ⅛ inch) diameter holes being typical.

FIG. 2 illustrates intermediate space 18 as an annular space that is formed between inner shell 14 and outer shell 12. Other geometries for intermediate space 18 are readily contemplated, depending on the geometry of inner shell 14 and outer shell 12 and their relative positioning (e.g., whether they are concentrically positioned or otherwise offset). Gas such as ozone-containing gas flowing into intermediate space 18 may be discharged from applicator 10 through at least one outlet 24 on outer shell 12. Outlet 24, like opening 22, may comprise a plurality of holes through outer shell 12 which may be configured (in terms of spacing, positioning, and length and direction of extension) as described above with respect to holes 22 on inner shell 14. Another exemplary outlet 24 or outer shell 12 is in the form of an elongated slot 24 that extends along at least a portion of the length of outer shell 12.

As with holes 22, described above, slot 24 may extend substantially linearly along a portion or section, in this case of outer shell 12, that is centered with respect to the overall length of outer shell 12. The length of this portion or section may be, for example, from about 30% to about 80%, and often from about 50% to about 70%, of the length of outer shell 12. According to an exemplary embodiment where the total length of the applicator (meaning the extended length if the applicator is extendible) is about 55 inches, the length of the slot is about 33 inches. Representative slot widths are from about 0.8 mm to about 6 mm (1/32 inches to about ¼ inches), with 1.5 mm (1/16 inches) being typical. Alternatively, slot 24 may extend non-linearly, such as in a helical or wave form on the surface of outer shell 12. The slot width may be adjusted, for example, using one or more adjustment screws 16 positioned on outer shell 12 that regulate the amount of force acting to close slot 24 (e.g., by tensioning a clamshell type closure). Other suitable hardware may be used for adjusting the width of slot 24, thereby providing an independent mechanism for controlling the linear velocity of gas exiting slot 24 of applicator 10 (i.e., with a smaller opening directionally increasing gas linear velocity for a given volumetric flow rate). In the case of melt curtain ozonation, fine adjustments to the flow rate of ozone-containing gas, by changing the width of slot 24, may be employed to obtain uniform gas distribution without disruption of the nearby melt curtain (or even to optimize this tradeoff).

As discussed above, the distribution of gas such as ozone-containing gas from slot 24 of applicator 10 is highly uniform, even in the case of applicator lengths exceeding about 24 inches. Exceptional distribution characteristics have been found to result when any of the applicators described herein having inner and outer shells is configured so that gas pressurized from interior space 20 is forced in different directions through opening 22 and outlet 24 before being discharged. That is, the gas flow direction through opening 22 does not coincide with that through outlet 24, and often these flows are in different directions. It may be desired to configure applicator 10 such that the flows through opening 22 and outlet 24 are in opposite directions. For example, as shown FIG. 2, gas flow from interior space 20 to intermediate space 18 is to the left, through opening 22 (e.g., a hole), whereas gas flow from intermediate space 18 to the exterior of applicator 10 is to the right, through outlet 24 (e.g., a slot). In this manner, the alignment of opening 22 and outlet 24 in opposite or substantially opposite directions significantly benefits the overall flow distribution of gas exiting applicator 10.

Figure 4:
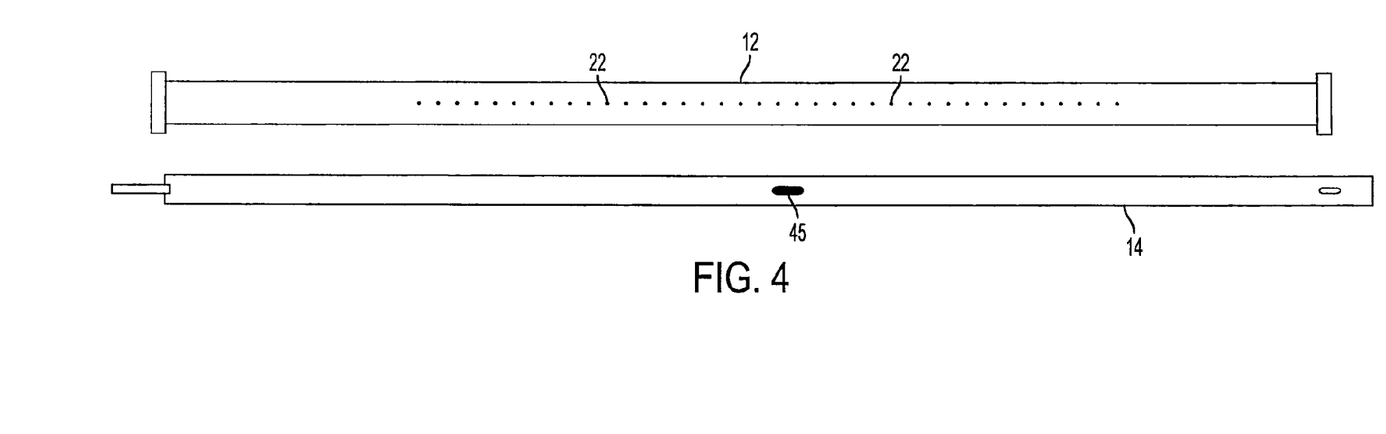
FIG. 4 depicts inner and outer shells of another representative ozone applicator.

FIG. 4 illustrates the use of an outlet on outer shell 12 in the form of a plurality of holes 22 distributed along a portion of the total length of outer shell 12. Holes 22 of outer shell in FIG. 4 may therefore be sized, spaced, and configured about the length of outer shell, in the same manner as discussed above with respect to inner shell 14. In the particular embodiment shown in FIG. 4, inner shell 14 has only one opening, namely a single elongated aperture 45 that can advantageously extend over the midpoint of the length of inner shell 14. In other embodiments, an inner shell having two, three, or more elongated apertures (e.g., extending in an axial line) centered about the length of the inner shell may also be used. A typical aperture 45, as an opening in inner shell 14 in the embodiment shown in FIG. 4, is elongated in the longitudinal or axial direction. A representative elongated aperture will have a length ranging from about 6 mm to about 25 mm (about ¼ inches to about 1 inch) and a width ranging from about 1.5 mm to about 6 mm (about 1/16 inches to about ¼ inches).

The central location of elongated aperture(s) provides a good distribution of gas exiting into the intermediate space and then discharging through the outlet of outer shell 12, for example the plurality of holes shown in FIG. 4. As discussed herein with respect to FIG. 2, the one or more openings (e.g., elongated aperture(s)) of inner shell 14 in the embodiment of FIG. 4 preferably do not align with openings such as holes 22 of outer shell 12. This increases the complexity of the gas flow path (i.e., by preventing gas in the intermediate space between shells from flowing without any encumbrance through a discharge opening) and thereby improves flow distribution. Preferably, the one or more elongated aperture openings of the inner shell are aligned substantially opposite the holes or other openings in the outer shell.

Figure 5:
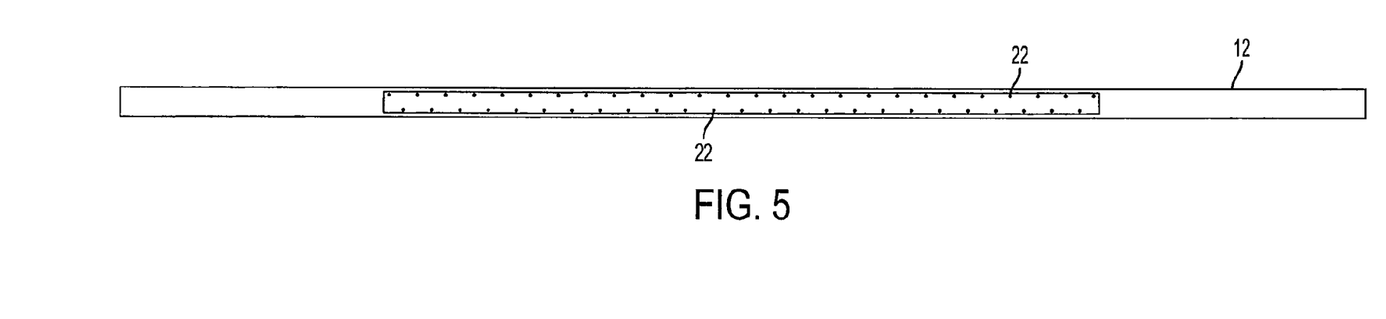
FIG. 5 depicts a single shell of a further representative ozone applicator.

FIG. 5 illustrates yet another embodiment of an ozone applicator with improved gas flow distribution. This embodiment lacks an inner shell, and instead utilizes a single elongated shell 12 that surrounds an interior space for receiving gas (e.g., containing ozone). The shell 12 has a plurality of openings for discharging this gas, with the openings being disposed about part of its surface. This part of the surface may be limited in its radial direction, axial direction, or both. For example, the axial or longitudinal dimension over which the holes 22 or other openings extend may be limited in the manner discussed above with respect to the plurality of holes extending along at least a portion (e.g., from about 30% to about 80%) of the length of inner shell 14 in the embodiment illustrated in FIG. 1, or along at least a portion of the length of outer shell 12 in the embodiment of FIG. 4. The plurality of openings or holes 22 in shell 12 can therefore be disposed along a portion of this length that is centered with respect to the total length of the shell. In terms of the radial or circumferential dimension of the surface over which the holes are disposed, this dimension preferably confines or limits the surface to an arcuate section within about 90° ($\pi/2$ radians), and often within about 45° ($\pi/4$ radians), based upon an arc of a cross-sectional shape (e.g., a circle) of the shell.

Figure 6:
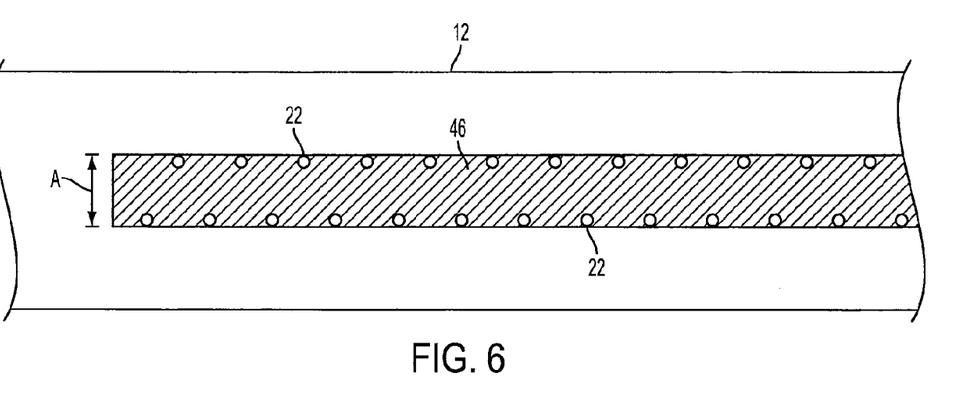
FIG. 6 depicts a close-up view of the single shell depicted in FIG. 5.
Figure 7:
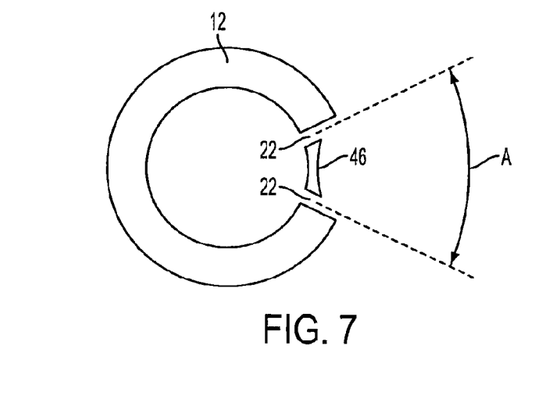
FIG. 7 depicts a cross-sectional view of the single shell depicted in FIG. 5.

FIG. 6 provides a close-up view of the features of shell 12 of the ozone applicator bar of FIG. 5. Holes 22 are disposed about a part 46 of the total surface area of shell 12. This part 46 of the total surface is confined to acute arc A, as shown in FIGS. 6 and 7, with this arc corresponding to a curved, circular section (or possibly a section of another cross-sectional shape of shell 12). The arc is normally that of an acute angle, and is often in the range from about 20° ($2\pi/9$ radians) to about 45° ($\pi/4$ radians). As is detailed in FIG. 7, the part 46 of the surface over which holes 22 are disposed may have a smaller thickness relative to that of the rest of shell 12. FIG. 7 shows a particular embodiment in which the part 46 of the surface having holes, or having boundaries defined by rows of holes, is a concave or curved surface, with the curvature being opposite the curvature of the rest of the surface of shell 12.

As is shown in the particular embodiment of FIG. 6, one line of holes 22 is radially spaced apart, by being separated by arc A, from another line of holes 22. Also, these separate, axially or longitudinally extending lines are disposed in a staggered conformation, such that the centers of holes 22 in each line are not at the same axial position about the length of shell 12. Instead, the centers of holes 22 of one line fall between the centers of holes of the separate line. In a preferred embodiment, the centers of one line of holes may, in the longitudinal direction, fall half-way between the centers of the separate line of holes. The hole diameters and hole spacing, as described above with respect to the embodiment comprising both inner and outer shells in FIG. 1, are appropriate with respect to the embodiment illustrated in FIG. 6.

Figure 8:
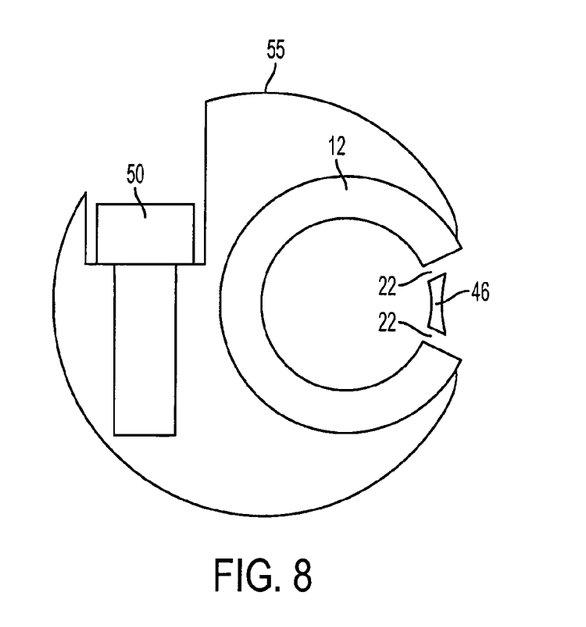
FIG. 8 depicts the use of a coupling or adapter for use with an ozone applicator having a relatively small outer diameter.

In the embodiment shown in FIG. 6, using a single elongated shell 12, the outer diameter of this shell may be reduced relative to the outer diameter of an outer shell used in the two-shell configuration, for example in the embodiment illustrated in FIG. 1. In this case, a coupling 50 may be used, as shown in FIG. 8, to adapt the smaller diameter shell 12 to a larger diameter receptacle or pocket 55. Coupling 50 therefore allows shell 12, having a diameter that is smaller than a conventional applicator, to be maintained in a fixed position in bracketing used for pocket 55 for mounting such a conventional applicator. A representative receptacle or pocket 55 may be designed to accommodate a conventional shell having an outer diameter from about 25 mm to about 32 mm (about 1 inch to about 1.25 inches), whereas a single exemplary shell, for example in the embodiment illustrated in FIGS. 6 and 7, may have an outer diameter of only about 19 mm (about ¾ inches). Coupling 50 can therefore be used to occupy some of the excess space between pocket 55 and shell 12 and also maintain a fixed position of shell 12 relative to a polymer melt curtain during ozonation.

Applicator bars described herein are suitable in polymer oxidation methods to improve the adhesion of a polymer to a substrate. According to such methods, a surface of the polymer (e.g., an essentially flat molten polymer extrudate) may be exposed to an ozone-containing gas discharged from any of the various applicators described above.

According to the particular polymer oxidation method known as melt curtain ozonation, ozone-containing gas, formed as a mixture of ozone gas and a diluent gas such as air, is routed to an ozone applicator such as those described above. The ozone gas is first formed, at concentrations discussed above, in an ozone generator according to known methods. Aspects of the invention are directed to methods and associated equipment for ensuring that a gas such as a diluent gas flows through the applicator continually during the ozonation process, even when ozone gas flow is stopped or interrupted. For example, ozone gas flow may be diverted from applicator during startup, shutdown, and non-normal operating periods over the course of the ozonation process, such as those associated with operational upsets and/or unsafe conditions. Apparatuses and methods associated with these aspects therefore ensure that gas flows through applicator 10 during ozonation even in the absence of ozone gas flow.

Figure 3:
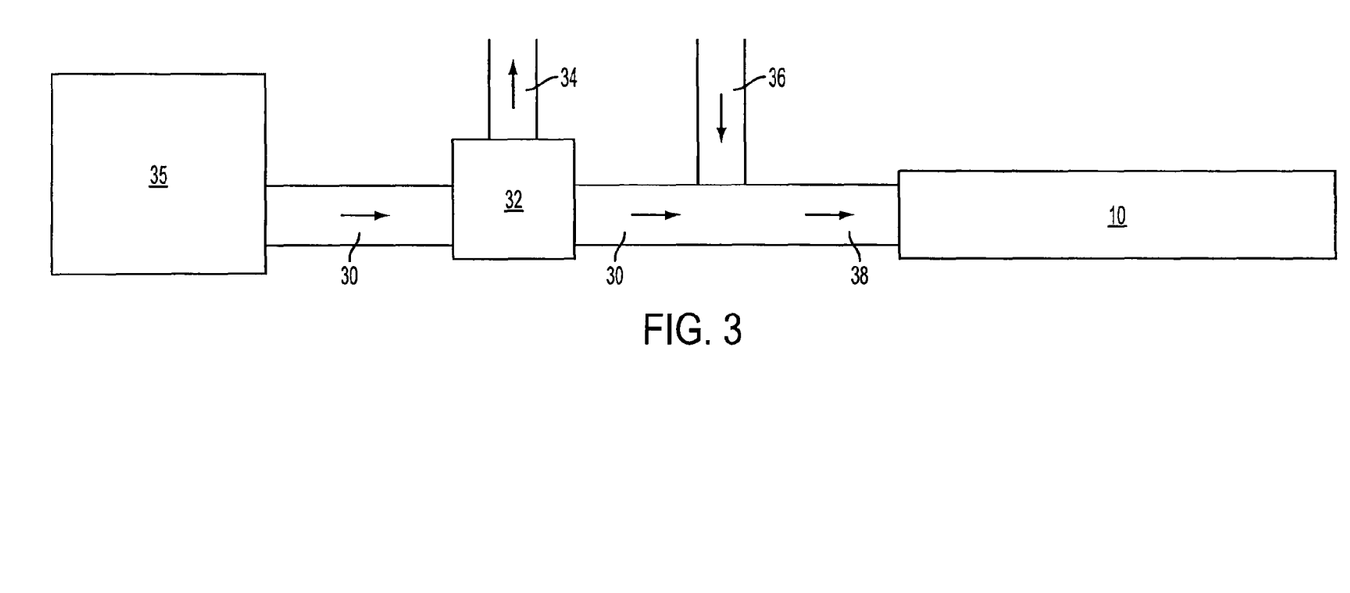
FIG. 3 depicts a flow configuration for gases to an ozone applicator.

Accordingly, a representative flow configuration used in equipment such as in an ozonation apparatus for flowing gases to an ozone applicator is depicted in FIG. 3. An ozone conduit 30 is used to flow ozone gas from an ozone generator 35 to an ozone applicator, such as the representative applicator 10 depicted in FIG. 1. A device 32 is positioned on ozone gas conduit 30 and acts on the ozone gas stream to interrupt or stop flow to the ozone applicator when necessary, such as under any of the non-normal operating periods discussed above. Device 32 may, for example, be a diverter valve to route ozone gas to a vent conduit 34 rather than allowing ozone gas to continue, in the case of normal operation, through ozone gas conduit 30. Device 32, which may be an automatically or manually actuated valve, is positioned and acts on flow through ozone gas conduit 30 between ozone generator and ozone applicator 10.

In the flow configuration depicted in FIG. 3, diluent gas conduit 36 flows diluent gas such as air to ozone applicator 10. As shown, diluent gas conduit 36 and ozone gas conduit 30 intersect or fluidly communicate, resulting in mixing of ozone gas and diluent gas to form ozone-containing gas in an ozone-containing gas conduit 38 upstream of applicator 10. This intersection or mixing occurs downstream of device 32, allowing diluent gas to be continually routed through applicator 10, independently of ozone gas. The diluent gas may be fed to ozone gas conduit 30 through a jet pump (not shown) or other type of gas moving equipment. As discussed above, the flow of diluent gas may be increased or decreased when ozone gas flow is interrupted, depending on the desired mode of operation and the need to maintain positive pressure on a molten polymer film in the vicinity of applicator 10. Importantly, the flow configuration allows continuous input of diluent gas through applicator 10.

Typical flow rates of ozone gas and diluent gas during normal operating periods range from 2.8 to 280 liters per minute (0.1 to 10 cubic feet per minute (CFM)), but vary significantly according to the particular application. Ratios of ozone gas:diluent gas flow rates often range from 1:10 to 10:1. Ozone applicators described above, which may have an inner shell disposed within an outer shell, or otherwise a single shell with a particular outlet opening configuration, improve gas distribution compared to conventional applicators, allowing for greater flexibility in processes involving gas distribution such as melt curtain ozonation.

For example, the use of these ozone applicators allows comparatively higher gas flows through the applicator, without resulting in detrimentally high back pressure in the ozone generator, which typically operates at slightly above atmospheric pressure (e.g., from about 0.2 barg to about 0.7 barg (about 3 to about 10 psig)). In one representative embodiment, a flow of 57 liters per minute (2 CFM) of ozone-containing gas through a conventional applicator may result in excessive ozone generator pressures, whereas a flow of 85-113 liters per minute (3-4 CFM) is possible through applicators described above, without exceeding the ozone generator pressure thresholds. According to various embodiments of the invention, a pressure regulator (e.g., a pressure relief valve) may be included in an ozonation apparatus to prevent excessive ozone generator pressures.

Additionally, ozone applicators described above provide improved gas distribution, for example across the width of a sheet of molten polymer, allowing for comparatively less air or other diluent to be charged to the applicator to achieve a desired degree of distribution (e.g., uniformity of oxidation of a molten polymer surface). Reduced diluent flow rates provide correspondingly increased ozone concentrations in ozone-containing gas discharged from the applicator and consequently improved oxidization of a polymer surface. Overall, therefore, a comparatively greater range of flow rates can be applied to applicators having (i) an inner and outer shell configuration with internal openings (e.g., elongated apertures or otherwise holes) and an outlet (e.g., in the form of a plurality of holes or otherwise an elongated slot), or otherwise (ii) a single shell configuration with a plurality of outlet openings as described above. Gas distribution is improved at low flow rates, while back pressure buildup is managed at high flow rates.

Ozone applicators as described herein thus provide a number of possible advantages, particularly in melt curtain ozonation processes, such as higher laminate production rates and improved product quality in terms of reduced delamination or greater force needed to separate the polymer from the substrate (e.g., paper) in the finished product. In view of the above, it will be seen that other advantages may be achieved and other advantageous results may be obtained. It will also be appreciated that the apparatuses and methods described above may be used with, or performed in conjunction with, conventional apparatuses and methods, such as those used for corona pre-treatment or flame pre-treatment. As various changes could be made in the above apparatuses and methods without departing from the scope of the present disclosure, it is intended that all matter contained in this application shall be interpreted as illustrative only and not limiting in any way the scope of the appended claims.

The following examples are set forth as representative of the present invention. These examples are not to be construed as limiting the scope of the invention as these and other equivalent embodiments will be apparent in view of the present disclosure and appended claims.

EXAMPLES

Various melt curtain ozonation studies were undertaken to compare the performance of an ozone applicator as described above and a conventional applicator. Overall testing conditions are summarized in Table 1 and specific operating parameters that were varied in each test are summarized in Tables 2A-2H.

TABLE 1

| 1 Roll | 1 Roll | Ozone Applicator Bars (2) |
|---|---|---|
| 32,000 ft | 60,000 ft | |
| 48RHB-12 | 48 ga 24CT PET | |
| PET | unctd, T1826"wide | |
| 25" wide | | |
| Makeready | | |
| Materials Needed: | | |

Mice A131X Primer, NA-204 or NA-214
XL LINE SET - UP
Die gap = .030"
Nip impression - ½'
CAAAC Plug or other as only one XL resin needed
NA214-Melt Temp - 605 F.
Qip, Temp-at-500 F. and 610 F. on edges
Airgap as specified
Ozonator:

$O_2$ = 60 scfh
Reactor Pressure = 4.5 psi
Incoming Air Pressure = 35 psi

TABLE 2A

Phase 1 - Ozone Value Displayed v/s Voltage and Added Air
Use Makeready Film (No Primer) for Phase 1
Part 1: Ozone Monitor in Normal (Current) Position (after added air B4 Applicator Bar)
Use Current Applicatort Bar
LDPE at Minimum coating weight and minimum linespeed

| Variable | % Voltage | Added Air | Record Displayed Value Ozone (g/Nm3) |
|---|---|---|---|
| 1 | 60 | 0 | |
| 2 | 70 | 0 | |
| 3 | 75 | 0 | |
| 4 | 80 | 0 | |
| 5 | 85 | 0 | |
| 6 | 90 | 0 | |
| 7 | 95 | 0 | |
| 8 | 100 | 0 | |
| 9 | 60 | 1 | |
| 10 | 70 | 1 | |
| 11 | 75 | 1 | |
| 12 | 80 | 1 | |
| 13 | 85 | 1 | |
| 14 | 90 | 1 | |
| 15 | 95 | 1 | |
| 16 | 100 | 1 | |
| 17 | 60 | 2 | |
| 18 | 70 | 2 | |
| 19 | 75 | 2 | |

TABLE 2A-continued

Phase 1 - Ozone Value Displayed v/s Voltage and Added Air
Use Makeready Film (No Primer) for Phase 1
Part 1: Ozone Monitor in Normal (Current) Position (after added air B4 Applicator Bar)
Use Current Applicatort Bar
LDPE at Minimum coating weight and minimum linespeed

| Variable | % Voltage | Added Air | |
|---|---|---|---|
| 20 | 80 | 2 | |
| 21 | 85 | 2 | |
| 22 | 90 | 2 | |
| 23 | 95 | 2 | |
| 24 | 100 | 2 | |
| | | | Record Ozone Value Displayed |
| 25 | 60 | 3 | |
| 26 | 70 | 3 | |
| 27 | 75 | 3 | |
| 28 | 80 | 3 | |
| 29 | 85 | 3 | |
| 30 | 90 | 3 | |
| 31 | 95 | 3 | |
| 32 | 100 | 3 | |

TABLE 2B

Part 2: Ozone Monitor Input at OP Side of Applicator Bar
LDPE at Minimum coating weight and minimum linespeed

| Variable | % Voltage | Added Air | |
|---|---|---|---|
| | | | Record Displayed Value Ozone (g/Nm3) |
| 40 | 60 | 0 | |
| 41 | 70 | 0 | |
| 42 | 75 | 0 | |
| 43 | 80 | 0 | |
| 44 | 85 | 0 | |
| 45 | 90 | 0 | |
| 46 | 95 | 0 | |
| 47 | 100 | 0 | |
| 48 | 60 | 1 | |
| 49 | 70 | 1 | |
| 50 | 75 | 1 | |
| 51 | 80 | 1 | |
| 52 | 85 | 1 | |
| 53 | 90 | 1 | |
| 54 | 95 | 1 | |
| 55 | 100 | 1 | |
| 56 | 60 | 2 | |
| 57 | 70 | 2 | |
| 58 | 75 | 2 | |
| 59 | 80 | 2 | |
| 60 | 85 | 2 | |
| 61 | 90 | 2 | |
| 62 | 95 | 2 | |
| 63 | 100 | 2 | |
| | | | Record Ozone Value Displayed |
| 64 | 60 | 3 | |
| 65 | 70 | 3 | |
| 66 | 75 | 3 | |
| 67 | 80 | 3 | |
| 68 | 85 | 3 | |
| 69 | 90 | 3 | |
| 70 | 95 | 3 | |
| 71 | 100 | 3 | |

TABLE 2C

Part 3: Ozone Monitor Input at OP Side of Conventional Applicator Bar
LDPE at Minimum coating weight and minimum linespeed

| Variable | % Voltage | Added Air | |
|---|---|---|---|
| | | | Record Displayed Value Ozone (g/Nm3) |
| 80 | 60 | 0 | |
| 81 | 70 | 0 | |
| 82 | 75 | 0 | |
| 83 | 80 | 0 | |
| 84 | 85 | 0 | |
| 85 | 90 | 0 | |
| 86 | 95 | 0 | |
| 87 | 100 | 0 | |
| 88 | 60 | 1 | |
| 89 | 70 | 1 | |
| 90 | 75 | 1 | |
| 91 | 80 | 1 | |
| 92 | 85 | 1 | |
| 93 | 90 | 1 | |
| 94 | 95 | 1 | |
| 95 | 100 | 1 | |
| 96 | 60 | 2 | |
| 97 | 70 | 2 | |
| 98 | 75 | 2 | |
| 99 | 80 | 2 | |
| 100 | 85 | 2 | |
| 101 | 90 | 2 | |
| 102 | 95 | 2 | |
| 103 | 100 | 2 | |
| | | | Record Ozone Value Displayed |
| 104 | 60 | 3 | |
| 105 | 70 | 3 | |
| 106 | 75 | 3 | |
| 107 | 80 | 3 | |
| 108 | 85 | 3 | |
| 109 | 90 | 3 | |
| 110 | 95 | 3 | |
| 111 | 100 | 3 | |

TABLE 2D

Part 4: Ozone Monitor Input at OP Side of Applicator Bar Design Slot Gap at .010"edges, .007" center
LDPE at Minimum coating weight and minimum linespeed

| Variable | % Voltage | Added Air | |
|---|---|---|---|
| | | | Record Displayed Value Ozone (g/Nm3) |
| 120 | 60 | 0 | |
| 121 | 70 | 0 | |
| 122 | 75 | 0 | |
| 123 | 80 | 0 | |
| 124 | 85 | 0 | |
| 125 | 90 | 0 | |
| 126 | 95 | 0 | |
| 127 | 100 | 0 | |
| 128 | 60 | 1 | |
| 129 | 70 | 1 | |
| 130 | 75 | 1 | |
| 131 | 80 | 1 | |
| 132 | 85 | 1 | |
| 133 | 90 | 1 | |
| 134 | 95 | 1 | |
| 135 | 100 | 1 | |
| 136 | 60 | 2 | |
| 137 | 70 | 2 | |
| 138 | 75 | 2 | |
| 139 | 80 | 2 | |
| 140 | 85 | 2 | |
| 141 | 90 | 2 | |

TABLE 2D-continued

Part 4: Ozone Monitor Input at OP Side of Applicator Bar Design
Slot Gap at .010"edges, .007" center
LDPE at Minimum coating weight and minimum linespeed

| Variable | % Voltage | Added Air | |
|---|---|---|---|
| 142 | 95 | 2 | |
| 143 | 100 | 2 | |
| | | | Record Ozone Value Displayed |
| 144 | 60 | 3 | |
| 145 | 70 | 3 | |
| 146 | 75 | 3 | |
| 147 | 80 | 3 | |
| 148 | 85 | 3 | |
| 149 | 90 | 3 | |
| 150 | 95 | 3 | |
| 151 | 100 | 3 | |

TABLE 2E

Part 5: Ozone Monitor Input at OP Feed with Applicator Bar (Dual Feed)
Slot Gap at .010" edge, .007" center
LDPE at Minimum coating weight and minimum linespeed

| Variable | % Voltage | Added Air | |
|---|---|---|---|
| | | | Record Displayed Value Ozone (g/Nm3) |
| 160 | 60 | 0 | |
| 161 | 70 | 0 | |
| 162 | 75 | 0 | |
| 163 | 80 | 0 | |
| 164 | 85 | 0 | |
| 165 | 90 | 0 | |
| 166 | 95 | 0 | |
| 167 | 100 | 0 | |
| 168 | 60 | 1 | |
| 169 | 70 | 1 | |
| 170 | 75 | 1 | |
| 171 | 80 | 1 | |
| 172 | 85 | 1 | |
| 173 | 90 | 1 | |
| 174 | 95 | 1 | |
| 175 | 100 | 1 | |
| 176 | 60 | 2 | |
| 177 | 70 | 2 | |
| 178 | 75 | 2 | |
| 179 | 80 | 2 | |
| 180 | 85 | 2 | |
| 181 | 90 | 2 | |
| 182 | 95 | 2 | |
| 183 | 100 | 2 | |
| | | | Record Ozone Value Displayed |
| 184 | 60 | 3 | |
| 185 | 70 | 3 | |
| 186 | 75 | 3 | |
| 187 | 80 | 3 | |
| 188 | 85 | 3 | |
| 189 | 90 | 3 | |
| 190 | 95 | 3 | |
| 191 | 100 | 3 | |

TABLE 2F

Phase 2 - Ozone/TIAG Adhesion
Structure - 48 ga PET/PEI/16# LDPE (NA-214)
NA214 Melt Temp - 590 F.
Die Temp at 590 F. and 595 F. on edges
Ozone at: 35 psi. O2 = 60 scfm, Added Air = 2 scfm, Reactor Pressure = 4.5
Phase 2
Insert Slip Sheet labeled with Variable Number.
Save Sample labeled with OP Side for Aged Adhesion Testing.
Part 1: Ozone Monitor Input at OP Side of Conventional Application Bar

| Variable | Linespeed | Airgap | Record Ozone Monitor (g/Nm3) | Voltage (%) | TIAG | Off-line Adhesion | Aged Adhesion |
|---|---|---|---|---|---|---|---|
| 200 | 400 | 9 | | 0 | 100 | | |
| 201 | 400 | 8.2 | | 0 | 90 | | |
| 202 | 400 | 7.4 | | 0 | 80 | | |
| 203 | 435 | 7.1 | | 0 | 70 | | |
| 204 | 510 | 7.1 | | 0 | 60 | | |
| 205 | 605 | 7.1 | | 0 | 50 | | |
| 206 | 760 | 7.1 | | 0 | 40 | | |
| 207 | 400 | 9 | | 70 | 100 | | |
| 208 | 400 | 8.2 | | 70 | 90 | | |
| 209 | 400 | 7.4 | | 70 | 80 | | |
| 210 | 435 | 7.1 | | 70 | 70 | | |
| 211 | 510 | 7.1 | | 70 | 60 | | |
| 212 | 605 | 7.1 | | 70 | 50 | | |
| 213 | 760 | 7.1 | | 70 | 40 | | |
| 214 | 400 | 9 | | 80 | 100 | | |
| 215 | 400 | 8.2 | | 80 | 90 | | |
| 216 | 400 | 7.4 | | 80 | 80 | | |
| 217 | 435 | 7.1 | | 80 | 70 | | |
| 218 | 510 | 7.1 | | 80 | 60 | | |
| 219 | 605 | 7.1 | | 80 | 50 | | |
| 220 | 760 | 7.1 | | 80 | 40 | | |
| 221 | 400 | 9 | | 90 | 100 | | |
| 222 | 400 | 8.2 | | 90 | 90 | | |
| 223 | 400 | 7.4 | | 90 | 80 | | |

TABLE 2F-continued

Phase 2 - Ozone/TIAG Adhesion
Structure - 48 ga PET/PEI/16# LDPE (NA-214)
NA214 Melt Temp - 590 F.
Die Temp at 590 F. and 595 F. on edges
Ozone at: 35 psi. O2 = 60 scfm, Added Air = 2 scfn, Reactor Pressure = 4.5
Phase 2
Insert Slip Sheet labeled with Variable Number.
Save Sample labeled with OP Side for Aged Adhesion Testing.
Part 1: Ozone Monitor Input at OP Side of Conventional Application Bar

| Variable | Linespeed | Airgap | Record Ozone Monitor (g/Nm3) | Voltage (%) | TIAG | Off-line Adhesion | Aged Adhesion |
|---|---|---|---|---|---|---|---|
| 224 | 435 | 7.1 | | 90 | 70 | | |
| 225 | 510 | 7.1 | | 90 | 60 | | |
| 226 | 605 | 7.1 | | 90 | 50 | | |
| 227 | 760 | 7.1 | | 90 | 40 | | |
| 228 | 1010 | 7.1 | | 90 | 30 | | |

TABLE 2G

Part 2: Ozone Monitor Input at OP Feed with Applicator Bar (Dual Feed)
Slot Gap at .010" edge, .007" center

| Variable | Linespeed | Airgap | Record Ozone Monitor (g/Nm3) | Voltage (%) | TIAG | Off-line Adhesion | Aged Adhesion |
|---|---|---|---|---|---|---|---|
| 229 | 400 | 9 | | 70 | 100 | | |
| 230 | 400 | 8.2 | | 70 | 90 | | |
| 231 | 400 | 7.4 | | 70 | 80 | | |
| 232 | 435 | 7.1 | | 70 | 70 | | |
| 233 | 510 | 7.1 | | 70 | 60 | | |
| 234 | 605 | 7.1 | | 70 | 50 | | |
| 235 | 760 | 7.1 | | 70 | 40 | | |
| 236 | 400 | 9 | | 80 | 100 | | |
| 237 | 400 | 8.2 | | 80 | 90 | | |
| 238 | 400 | 7.4 | | 80 | 80 | | |
| 239 | 435 | 7.1 | | 80 | 70 | | |
| 240 | 510 | 7.1 | | 80 | 60 | | |
| 241 | 605 | 7.1 | | 80 | 50 | | |
| 242 | 760 | 7.1 | | 80 | 40 | | |
| 243 | 400 | 9 | | 90 | 100 | | |
| 244 | 400 | 8.2 | | 90 | 90 | | |
| 245 | 400 | 7.4 | | 90 | 80 | | |
| 246 | 435 | 7.1 | | 90 | 70 | | |
| 247 | 510 | 7.1 | | 90 | 60 | | |
| 248 | 605 | 7.1 | | 90 | 50 | | |
| 249 | 760 | 7.1 | | 90 | 40 | | |
| 250 | 1010 | 7.1 | | 90 | 30 | | |

TABLE 2H

Part 3: Coating Weight/Minimum Ozone versus Adhesion
Ozone Monitor Input at OP Feed with Applicator Bar (Dual Feed) Slot Gap at .010" edge, .007" center

| Variable | Linespeed | Airgap | Record Ozone Monitor (g/Nm3) | Voltage (%) | Coating Weight | TIAG | Off-line Adhesion | Aged Adhesion |
|---|---|---|---|---|---|---|---|---|
| 301 | 610 | 7.1 | | 0 | 10 | 60 | | |
| 302 | 610 | 7.1 | | 70 | 10 | 60 | | |
| 303 | 605 | 7.1 | | 70 | 10 | 60 | | |
| 304 | 760 | 7.1 | | 70 | 10 | 40 | | |
| 305 | 510 | 7.1 | | 80 | 10 | 60 | | |
| 306 | 605 | 7.1 | | 80 | 10 | 50 | | |
| 307 | 760 | 7.1 | | 80 | 10 | 40 | | |
| 308 | 1010 | 7.1 | | 80 | 10 | 30 | | |
| 309 | 1010 | 7.1 | | 80 | 10 | 30 | | |
| 310 | 1010 | 7.1 | | 80 | 10 | 30 | | |

What is claimed is:

1. A method of ozonating a melt curtain, the method comprising:

mixing ozone gas from an ozone gas generator with a diluent gas downstream of a device, wherein said device is both disposed downstream of said ozone gas generator and configured to selectively interrupt or stop a flow of ozone gas toward an ozone applicator;

flowing a mixture comprising said ozone gas and said diluent gas into said ozone applicator, wherein said ozone applicator comprises an elongated inner shell disposed within an elongated outer shell, wherein said inner shell surrounds an interior space that receives said mixture and has at least one opening for flowing said mixture from said interior space into an intermediate space formed between said inner shell and said outer shell, and said outer shell has an outlet in the form of a plurality of openings for discharging said mixture from said applicator; and discharging said mixture in the vicinity of a side of a melt curtain.

2. The method of claim 1, wherein said device is a manually or automatically actuated valve.

3. The method of claim 1, further comprising interrupting or stopping the flow of ozone gas toward said applicator without interrupting or stopping diluent gas flow to said applicator.

4. The method of claim 1, further comprising flowing said diluent gas into said applicator in the absence of ozone gas during a non-normal operating period.

5. The method of claim 1, wherein said diluent gas is air.

6. The method of claim 1, wherein said melt curtain is configured to adhere to a substrate.

7. The method of claim 1, wherein said melt curtain is configured to adhere to an intermediate layer that adheres to a substrate.

* * * * *